(12) United States Patent
Rothenberg

(10) Patent No.: US 10,138,455 B2
(45) Date of Patent: Nov. 27, 2018

(54) INCUBATOR CHAMBER

(71) Applicant: Billups-Rothenberg, Inc., San Diego, CA (US)

(72) Inventor: Barry E. Rothenberg, Del Mar, CA (US)

( * ) Notice: Subject to any disclaimer, the term of this patent is extended or adjusted under 35 U.S.C. 154(b) by 48 days.

(21) Appl. No.: 15/071,144

(22) Filed: Mar. 15, 2016

(65) Prior Publication Data
US 2016/0194596 A1 Jul. 7, 2016

Related U.S. Application Data

(63) Continuation of application No. 14/094,641, filed on Dec. 2, 2013, now Pat. No. 9,315,769.

(60) Provisional application No. 61/735,844, filed on Dec. 11, 2012.

(51) Int. Cl.
| | | |
|---|---|---|
| *C12M 1/00* | (2006.01) | |
| *C12M 1/04* | (2006.01) | |
| *C12M 1/14* | (2006.01) | |
| *B01L 1/00* | (2006.01) | |
| *C12M 3/00* | (2006.01) | |

(52) U.S. Cl.
CPC ............ *C12M 41/14* (2013.01); *C12M 23/38* (2013.01); *C12M 23/46* (2013.01); *C12M 29/24* (2013.01); *Y10T 137/6851* (2015.04)

(58) Field of Classification Search
CPC ............................... C12M 21/14; C12M 23/26
USPC ...................................................... 435/303.2
See application file for complete search history.

(56) References Cited

U.S. PATENT DOCUMENTS

| | | | |
|---|---|---|---|
| 3,886,047 A | | 5/1975 | Billups, Jr. |
| 4,301,252 A | | 11/1981 | Baker |
| 5,352,414 A | * | 10/1994 | Rothenberg ............ B01L 7/00 422/534 |
| 5,425,921 A | | 6/1995 | Coakley |
| 5,564,175 A | * | 10/1996 | Nejad ................ B25B 27/0028 29/235 |
| 5,823,340 A | | 10/1998 | Maihofer |
| 8,822,204 B2 | | 9/2014 | Tsuchiya |

OTHER PUBLICATIONS www.stemcell.com; Hypoxia Incubator Chamber; Chamber for Generation of a Hypoxic Environment for Tissue Cultue; downloaded from internet on Dec. 10, 2012.
www.hypoxiaincubator.com; Hypoxia Incubator; Billups-Rothenberg; downloaded from internet on Dec. 10, 2012.
www.jove.com; The Journal of Visualized Experiments (JoVE); Induction and Testing of Hypoxia in Cell Culture; Danli Wu, Patricia Yotnda; Center for Cell and Gene Therapy, Baylor College of Medicine; downloaded from internet on Dec. 10, 2012.

* cited by examiner

*Primary Examiner* — Kevin Joyner
*Assistant Examiner* — Holly M Mull

(57) ABSTRACT

A incubator chamber comprises a base, lid and plurality of trays, each of which are stackable upon one another in an open or closed configuration. A clamp could be provided having an interior cavity sized and dimensioned to simultaneously receive a portion of a perimeter of each of a base and a lid.

19 Claims, 9 Drawing Sheets

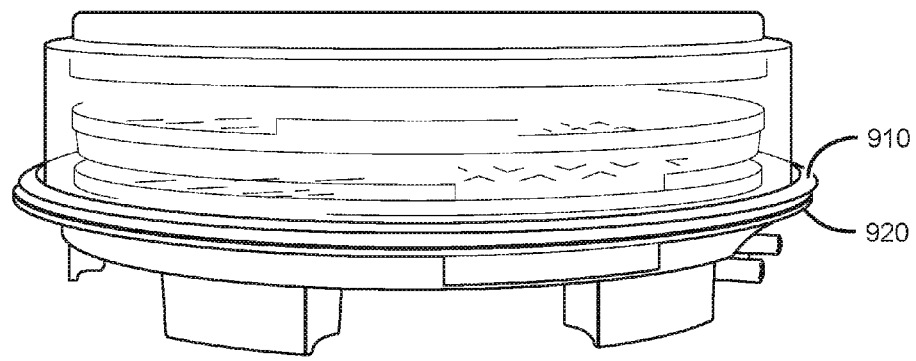
FIG. 9
FIG. 10
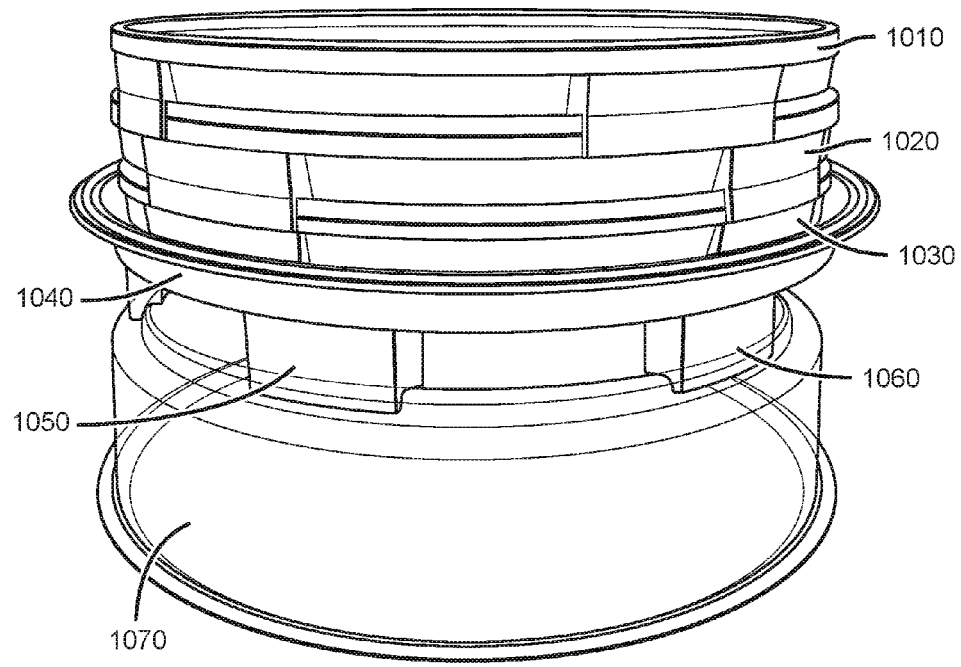

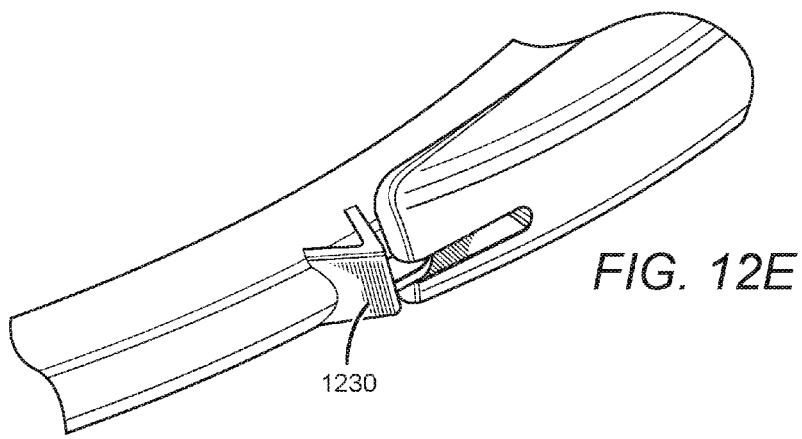
FIG. 12E
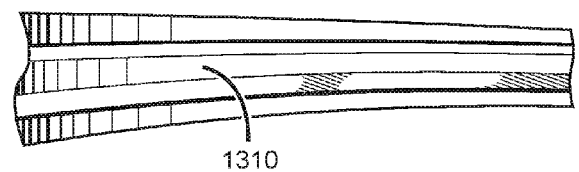
FIG. 13
FIG. 14
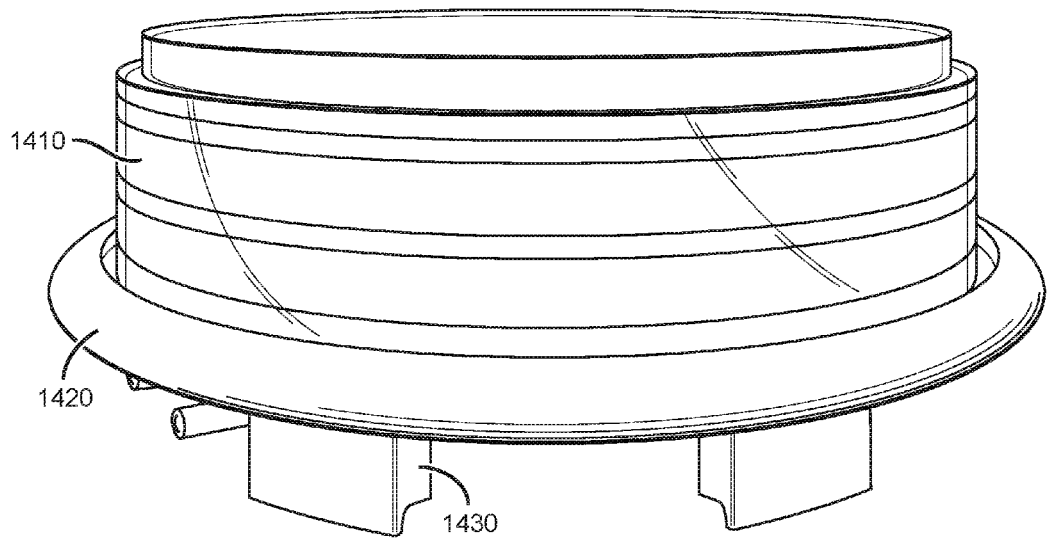

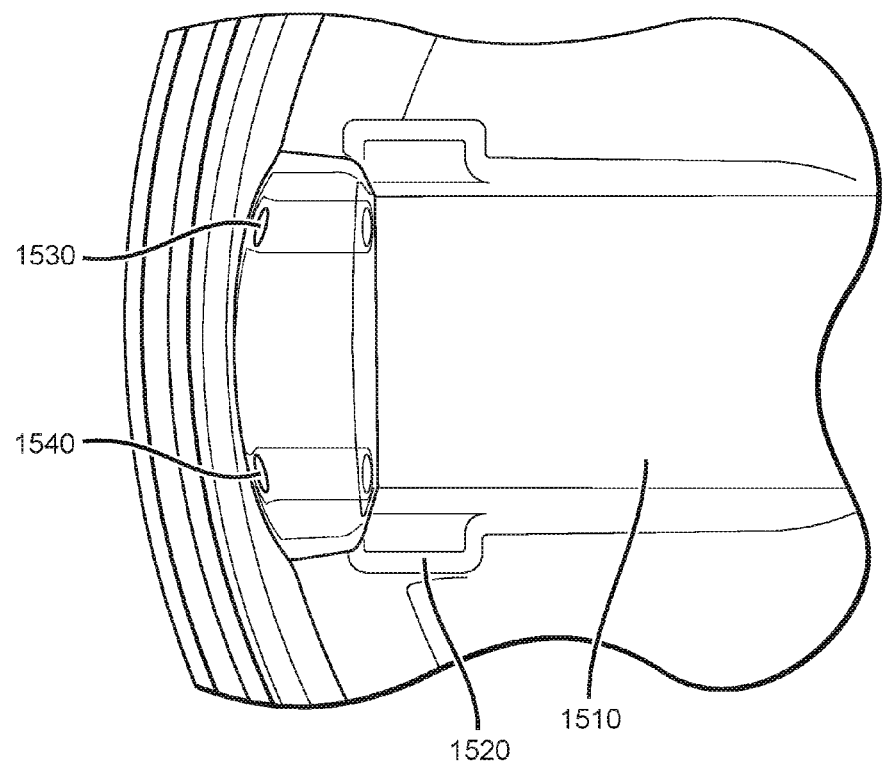
FIG. 15
FIG. 16
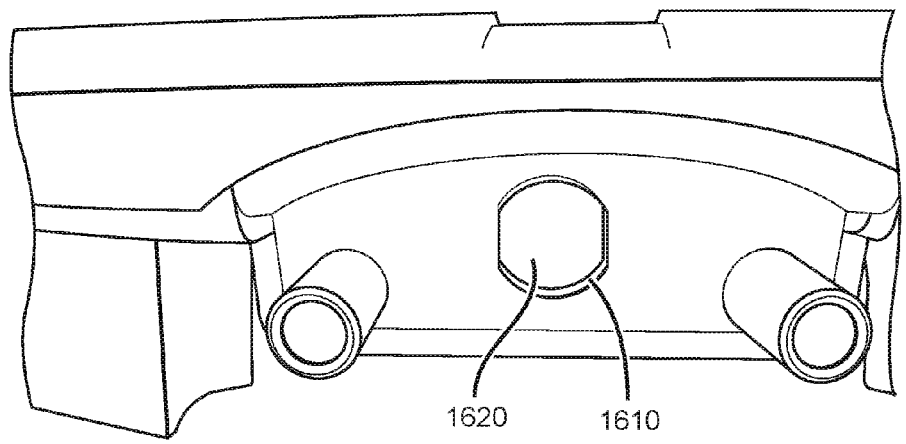

INCUBATOR CHAMBER

This application is a continuation of U.S. patent application having Ser. No. 14/094,641, filed on Dec. 2, 2013, which claims the benefit of priority to U.S. Provisional Application having Ser. No. 61/735,844 filed on Dec. 11, 2012. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is incubator chambers.

BACKGROUND

The following description includes information that may be useful in understanding the present invention. It is not an admission that any of the information provided herein is prior art or relevant to the presently claimed invention, or that any publication specifically or implicitly referenced is prior art.

The current inventor has developed numerous prior hypoxia incubator chambers, see e.g., http://www.stemcell.com/en/Products/All-Products/Hypoxia-Incubator-Chamber.aspx; http://www.hypoxiaincubator.com/; and http://www.jove.com/video/2899/induction-and-testing-of-hypoxia-in-cell-culture. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Unfortunately, previously developed chambers generally suffer from numerous disadvantages. For example, previously known chambers often have gas ports that extend well beyond the perimeter of the other components of the chamber, and can thus be easily damaged. Furthermore, many of the previously developed chambers are difficult to operate and fail to provide a desired level of modularity, functionality and convenience. Still further, functional tolerances in known products can be difficult to obtain and maintain.

Thus, there is still a need for improved incubator chambers and clamps.

SUMMARY OF THE INVENTION

The inventive subject matter provides apparatus, systems and methods in which an incubator chamber including a base and a lid provides an atmosphere-controlled environment. The base and lid could advantageously be sized and dimensioned to mate with one another in various ways to provide an optimum level of modularity.

In some aspects of the inventive subject matter, a base of an incubator chamber comprises one or more legs (e.g., 1, 2, 4, 6, 8, etc.) and a flange extending along at least a portion of a perimeter of the base (e.g., at least 25%, at least 50%, at least 75%, or even 100% of the perimeter). The base could also include an indentation, preferably disposed on the flange, which is sized and dimensioned to receive a sealing ring. The base could further comprise a depression on a portion on or adjacent the indentation, which could allow for simple removal of the sealing ring. Furthermore, a gas distribution portion (e.g., a ramp, pin or mesh, etc.) and one or more ports could be provided that allow for an atmosphere-controlled or monitored environment.

A lid of an incubator chamber of the inventive subject matter could comprise a top portion and a bottom portion, and the bottom portion could comprise a flange that is sized and dimensioned to mate (e.g., contact or couple) with at least one of a base flange and a base sealing ring to provide an air-tight incubator system, especially when the base and lid are locked together via a clamp. It is contemplated that when an incubator chamber is in an upright position, and the base and lid are coupled to provide a seal via their respective flanges, a gas port of a base could be sized and positioned such that the base and lid flange extend above and beyond the gas port, thereby protecting the gas port from a downward force.

In some embodiments, a top portion of the lid could comprise a tiered brim, and one or more legs of the base could comprise a shape complementary to the brim (e.g., an r-shaped bottom complementary to a tier of the brim, etc.). In such embodiments, the brim could prevent a movement of the base (e.g., sideways, etc.) when seated on the top portion of the lid. In other embodiments, the brim could comprise an indentation while one or more legs could comprise a knob, hook or other protrusion configured to lock with the indentation.

In yet another aspect of the inventive subject matter, a communication port (e.g., a wire port, a power port, etc.) could be provided that acts as an interface between an environment within the chamber and an environment exterior to the chamber. Furthermore, a port could comprise a self-sealing member to allow one or more objects to be placed in, and removed from, the incubator chamber without breaking a gas-tight seal.

An incubator chamber of the inventive subject matter could further comprise one or more trays (e.g., 1, 2, 3, 4, 5, 10, etc.) configured to stably stack upon one another. Preferably, at least a bottom tray could comprise one or more legs (e.g., 1, 2, 3, 4, 5, 10, etc.) that cooperates with a portion of a base to prevent a rotation of the bottom tray. For example, the base could comprise a gas distribution ramp, and the bottom tray could comprise two legs sized and dimensioned to sit on opposite sides of the gas distribution ramp. Additionally or alternatively a top tray could be sized and dimensioned to mate with a tier of a lid brim (or other narrowed portion of a lid) such that the tier acts as a ceiling to prevent vertical movement of one or more trays in the incubator chamber.

In another aspect of the inventive subject matter, a clamp could be provided to cooperate with at least a portion of each of a flange of a lid and a flange of a base. Viewed from another perspective, the clamp could include an inner perimeter cavity sized and dimensioned to concurrently receive the lid flange and base flange, or portions thereof. In some embodiments, the clamp could include a closure (e.g., a levered locking mechanism) that tightens the clamp about the flanges to approximate the base with the lid. The closure could comprise a catch (e.g., on a ring portion thereof, etc.) and a catch receiving portion (e.g., on a handle portion of the closure, etc.) such that the clamp could be releasably locked in a closed position.

In other aspects of the inventive subject matter, a gas distribution portion could comprise a ramp having an outer wall, and one or more of the ports could be positioned on the outer wall. Additionally or alternatively, the gas distribution portion could include, or be lateral to, a sensor seat configured to hold a sensor (e.g., a CO2 sensor, etc.). It is contemplated that a sensor (or any other object) could be inserted into the incubator chamber via removal of the lid or placement through a self-sealing membrane disposed at a port.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 9 is a side perspective view of a base and lid enclosing a plurality of trays.

FIG. 10 illustrates a lid being used as a pedestal for a base.

FIGS. 12A-12E show different view of a clamp of the inventive subject matter.

FIG. 13 shows an inner surface of a clamp.

FIG. 14 shows a clamp used with a base and lid of the inventive subject matter.

FIG. 15 is a partial top view of a base of the inventive subject matter showing a ramp.

FIG. 16 shows a port of the inventive subject matter.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The present invention provides for highly modular incubator chambers that could provide an atmosphere-controller environment. The incubator chamber could comprise a base, a lid, and a plurality of trays, which could each be stacked upon one another in both closed and open configurations.

It should be appreciated that some or all of the surfaces of a base, lid or any other component of an incubator chamber of the inventive subject matter can comprise rounded inner corners (as opposed to sharp corners) configured to facilitate cleaning of the incubator chamber, and thereby diminish the chance of contamination. Bases, lids, inlets, legs and other components of all suitable sizes, shapes and materials are contemplated. Suitable shapes include for example, circular, cylindrical, substantially U-shaped, tube-shaped, rectangular, spherical, or any other suitable shape. A preferred material is polycarbonate because it is both easy to clean and transparent at visible wavelengths, so an operator can see inside the device. However, any other suitable material or materials can be used, including for example, steel and aluminum.

Figure 1:
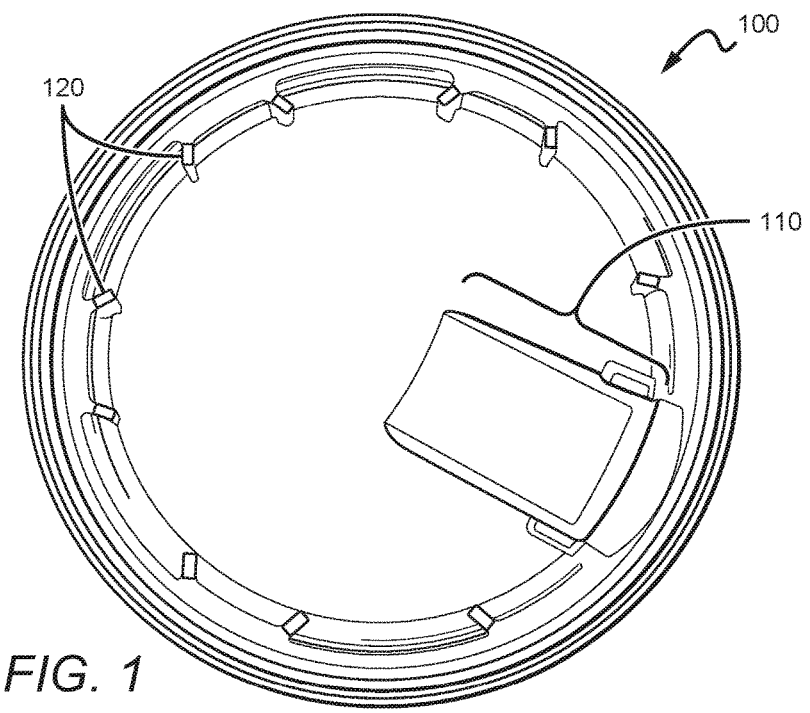
FIG. 1 is a top view of an incubator chamber of the inventive subject matter.

FIG. 1 illustrates an exemplary base of the inventive subject matter. Base 100 comprises, among other things, a plurality of ribs 120 configured to prevent a rotation of a tray (discussed further below), and a gas distribution portion 110. A gas distribution portion could comprise a ramp, pins, mesh or any other suitable portion that can be used to distribute the gas within the chamber. As illustrated here, gas distribution portion 110 comprises an upwardly curved ramp having first and second substantially triangular side walls, and an outer wall including first and second gas ports (e.g., gas inlet, gas outlet, etc.). In some embodiments, a height of the outer wall comprises a height of the ramp.

Gas ports of the inventive subject matter could be used to introduce or remove a gas from the incubator chamber. A Y-port could be coupled with a single gas inlet port and configured to deliver two separate streams of gas to the chamber. Each stream of gas could comprise a single gas, e.g. Oxygen, Carbon dioxide, Nitrogen, etc. or can comprise a mixture of gases, e.g., approximately 95% Oxygen and approximately 5% Carbon dioxide, or approximately 95% Nitrogen/approximately 5% Carbon dioxide, or any other suitable mixture of gases (e.g., 90%:10%, 85%:15%, 90%:5%:5%, etc.) to create an atmosphere-controlled environment. Also contemplated are one or more flow meters, which could be coupled to the Y-port or other port. A first gas could flow through a first flow meter, a second gas could flow through a second flow meter, and the combination of gasses could combine at the Y-port before entering the incubator chamber. Additionally or alternatively, a monitor could be provided (e.g., between the Y-port and the incubator chamber or any other location), which could measure oxygen or other gas concentrations.

When one or more gases enters the chamber via a port, the gas distribution member can disrupt air flow or force gases to mix rapidly (flush) prior to exiting (e.g., via the second port). Where the member is a ramp, it is contemplated that a height of the ramp can be at least 5%, at least 10%, at least 25%, or at least 50% or even more of a length of the ramp. Where delivery of a gas stream is complete, it is contemplated that a port can be closed in any suitable matter, including for example, a Tygon™ clamp, a clamping of a rubber tip of a port, a cap, or a valve. Additionally or alternatively, one or more of the ports could comprise a self-sealing membrane.

Figure 2:
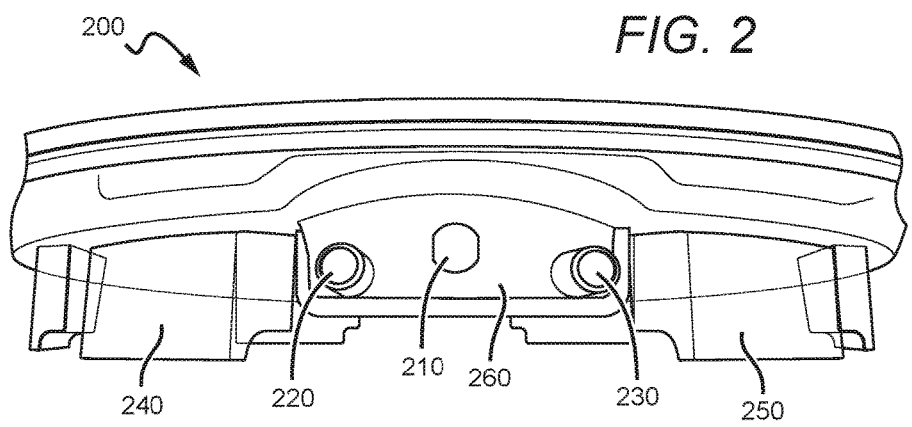
FIG. 2 is a side view of the incubator chamber of FIG. 1.

FIG. 2 shows a side partial view of a base of the inventive subject matter. Base 200 comprises a gas distribution portion 260 having an outer wall including a port 210 (e.g., wire, power or communication port, etc.), a gas inlet 220, and a gas outlet 230. Port 210 could be, among other things, configured to receive wires coupling an electronic detector (e.g., a sensor, etc.), disposed within a base, with an electronic reader (e.g., a sensor reader, etc.), disposed outside of the chamber. Base 200 further comprises first and second legs 240 and 250, respectively on opposite sides of gas distribution portion 260. As discussed above, base 200 could comprise a plurality of ribs on an interior surface, which is configured to prevent a rotation of a tray (as shown in FIG. 3).

Figure 3:
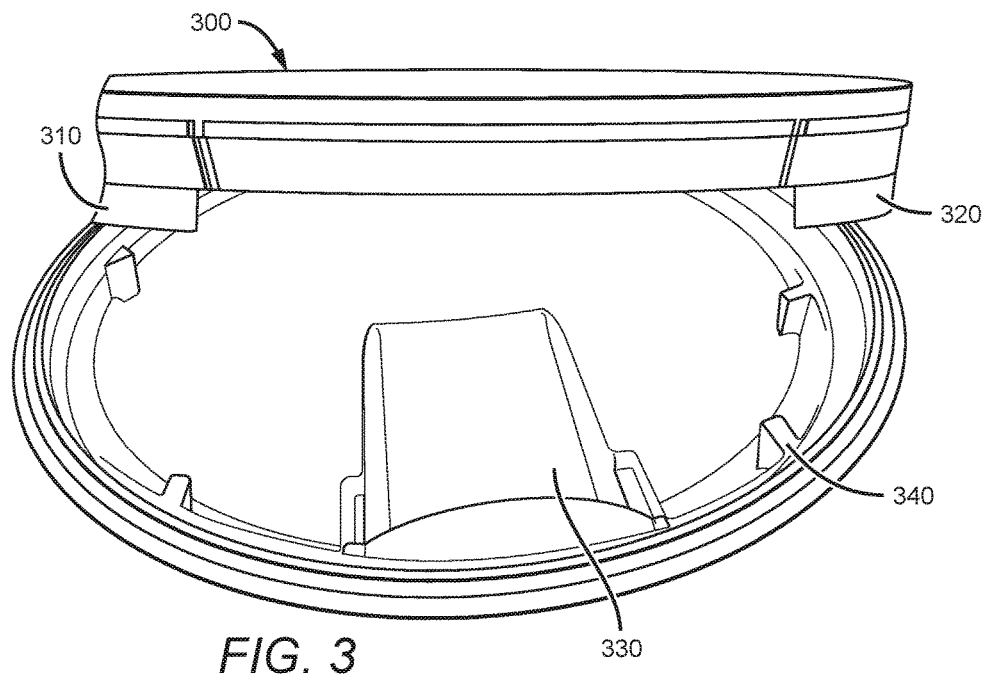
FIG. 3 illustrates a tray and base of the inventive subject matter.

FIG. 3 shows a base including gas distribution portion 330, and a plurality of ribs 340. Also shown is tray 300, which includes a plurality of legs (e.g., 310, 320, etc.) which are sized and dimensioned to be placed between (a) two or more ribs 340, or (b) between a rib 340 and gas distribution portion 330. Such placement of legs 310 and 320 allow at least one of ribs 340 and gas distribution portion 330 to restrict a rotation of tray to less than 45 degrees, preferably to less than 25 degrees, more preferably to less than 15 degrees, and even more preferably to less than 10 degrees.

Figure 4:
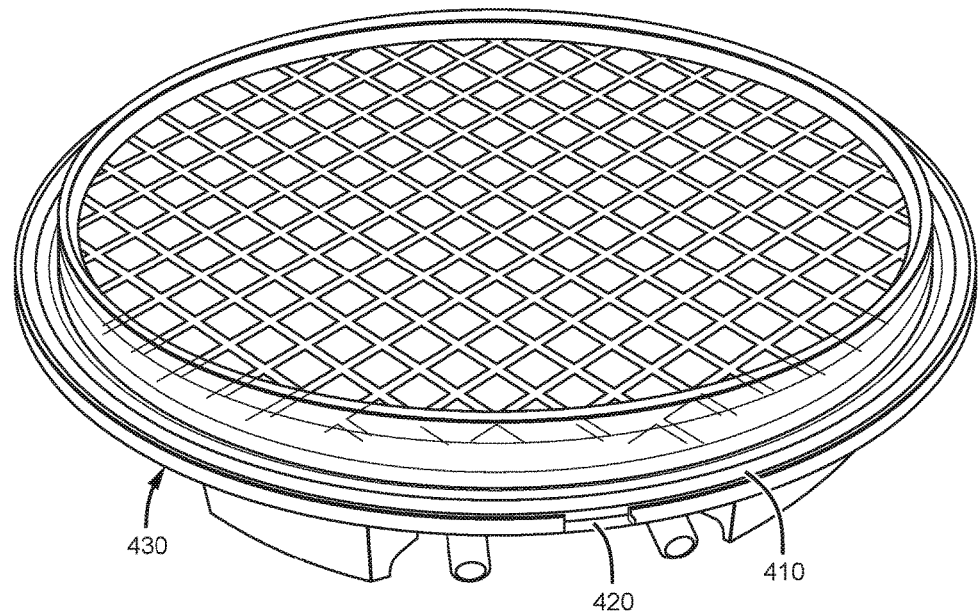
FIG. 4 illustrates a base having a flange, sealing ring and depression for removing the sealing ring.

FIG. 4 shows an embodiment of a base of the inventive subject matter holding a tray 430. The base comprises a flange extending across an entire perimeter thereof, and the flange includes an annular indentation sized and dimensioned to receive a sealing ring 410 (e.g., a rubber sealing ring, etc.). The flange could include a depression 420 adjacent to the indentation, which advantageously allows a user to conveniently remove sealing ring 410 from its respective annular indentation.

It should be noted that a flange need not be continuous around a perimeter of a base or lid (or portions thereof). For example, a lid or a base could include a series of flanges that extend around different portions of the lid or base's perimeter.

Figure 5:
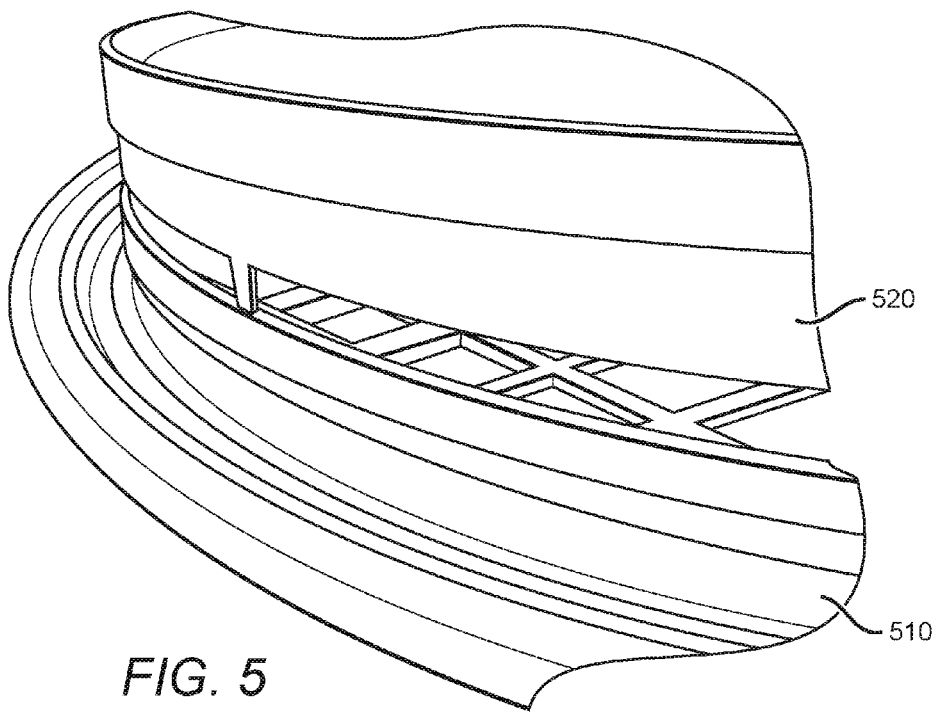
FIG. 5 illustrates two trays stably stacked upon one another.

FIG. 5 shows first and second trays, 510 and 520, respectively, which are stably stacked upon one another, and partially placed within a base. One or more of the trays could be supported by a base having a larger inner diameter than at least one of the trays. Tray 520 comprises a bottom portion including a plurality of legs, which are sized and dimensioned to mate with a top portion of tray 510. It is contemplated that a bottom portion of one tray could be complementary to a top portion of a second tray in any suitable manner. For example, a top portion could comprise an upwardly and vertically extending outer portion having a first diameter, and a bottom portion could comprise a downwardly and vertically extending perimeter portion having a second diameter smaller than the first diameter such that the entire downwardly extending portion fits within an upwardly extending portion. Additionally or alternatively, a downwardly extending portion could comprise a plurality of downwardly extending ribs along an annular portion having a diameter smaller than the upwardly extending perimeter portion.

One should appreciate that while the description herein is generally directed to incubator chambers having a substantially cylindrical interior shape, an incubator chamber of the inventive subject matter could comprise any suitable shape, size and number of components (e.g., trays, legs, etc.).

Figure 6:
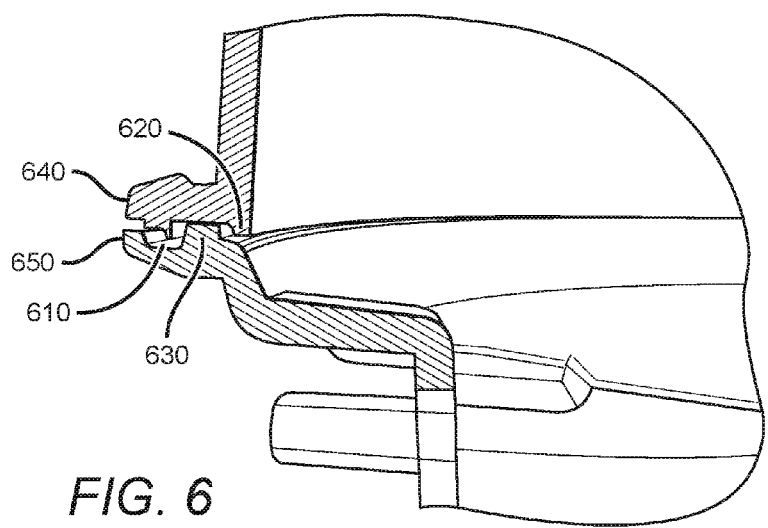
FIG. 6 is a partial cross-sectional view of a base and a lid.

FIG. 6 is a cross-sectional view of a portion of an incubator chamber of the inventive subject matter. As illustrated, the base comprises a flange 650 including a rim 630, and perimeter indentation 610, while the lid comprises a top flange 640 and a skirt 620. Each of the flanges 640, 650, rim and skirt extend along an entire perimeter of its respective component (e.g., base, lid, etc.), and rim 630 and skirt 620 couple together to prevent a horizontal sliding of the lid with respect to the base.

Figure 7:
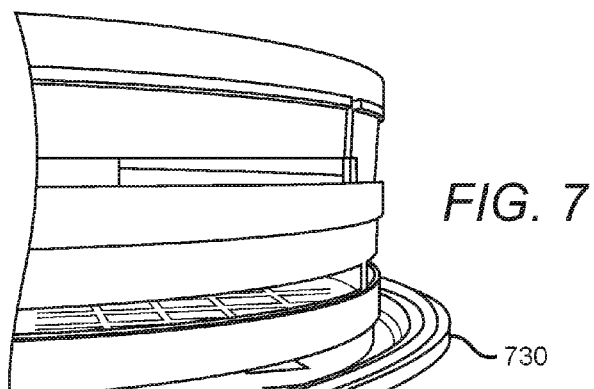
FIG. 7 illustrates a base having a flange overlying gas ports of the inventive subject matter.

FIG. 7 is a partial view of a base of the inventive subject matter, illustrating that a base flange 730 could extend sufficiently outwardly to completely overlie a port of the inventive subject matter. Here, flange 730 entirely overlies a gas inlet 710 and gas outlet 720 (e.g., first and second ports, respectively).

Viewed from another perspective, one or more ports could be located beneath a flange of the base, such that the ports do not extend beyond an outer perimeter of the base flange. In other words, a chamber could comprise a base having a flange, and one or more ports can be recessed in a wall of the base at a position inferior to the flange such that a likelihood of breaking of the port(s) is eliminated or reduced.

Figure 8A:
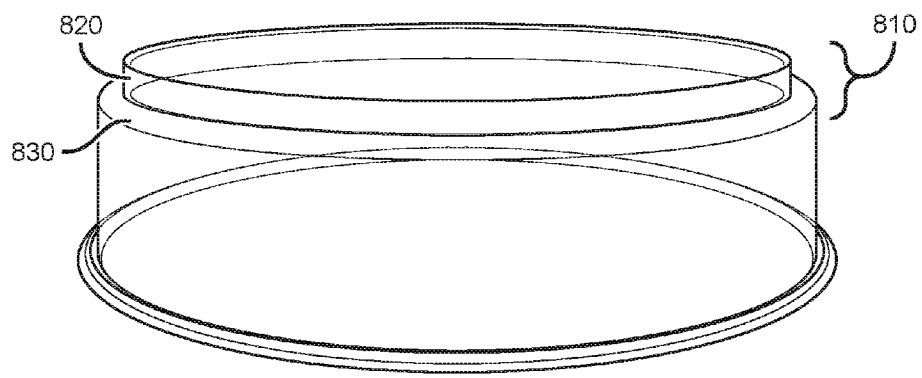
FIGS. 8A-8B are side perspective and close up views of a lid having a brim.
Figure 8B:
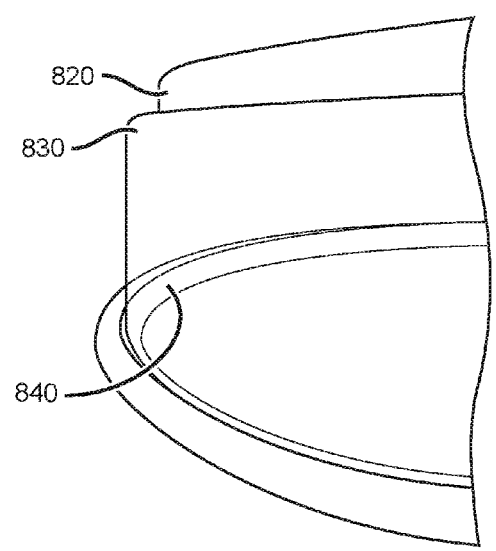

FIGS. 8A-8B show a lid of the inventive subject matter including a brim 810 (e.g., a substantially L-shaped portion, etc.). As illustrated, a diameter of a base flange is substantially equal to a diameter of the lid flange (e.g., within 10%, within 5%, within 1%, etc.). The lid includes a skirt 840 similar to skirt 620 of FIG. 6, and further includes a brim 810 having a superior portion 820 and inferior portion 830 (e.g., a top-tier surface, and a lower-tier surface). As previously described, a corresponding base could include legs, each having a bottom shape (e.g., a substantially r-shape, a partially raised bottom portion, etc.) that is configured to mate with superior portion 820 (or other portion) to prevent a base from sliding off the lid when placed thereon. The legs of a base are preferably between 1 cm and 5 cm, and more preferably between 2 cm and 3 cm in length. However, all suitable lengths are contemplated.

Figure 11:
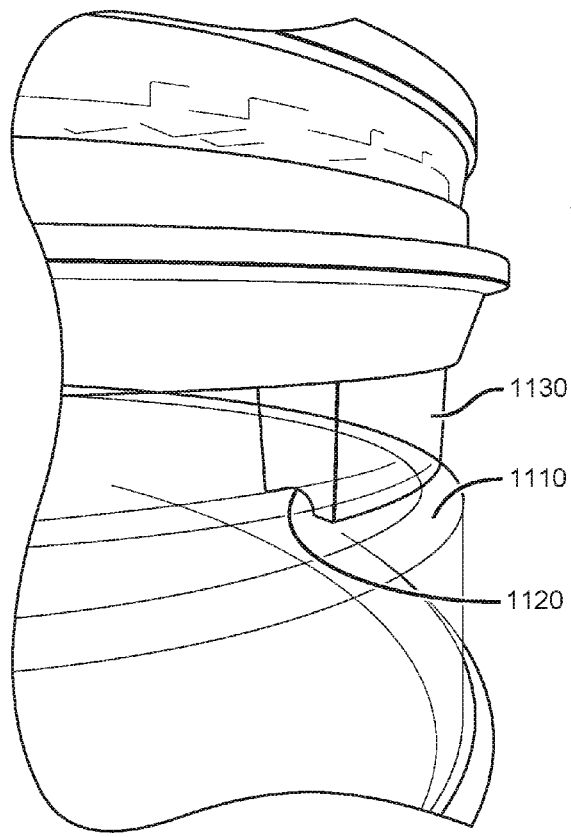
FIG. 11 is a close up view of a base leg interacting with a lid brim.
Figure 12A:
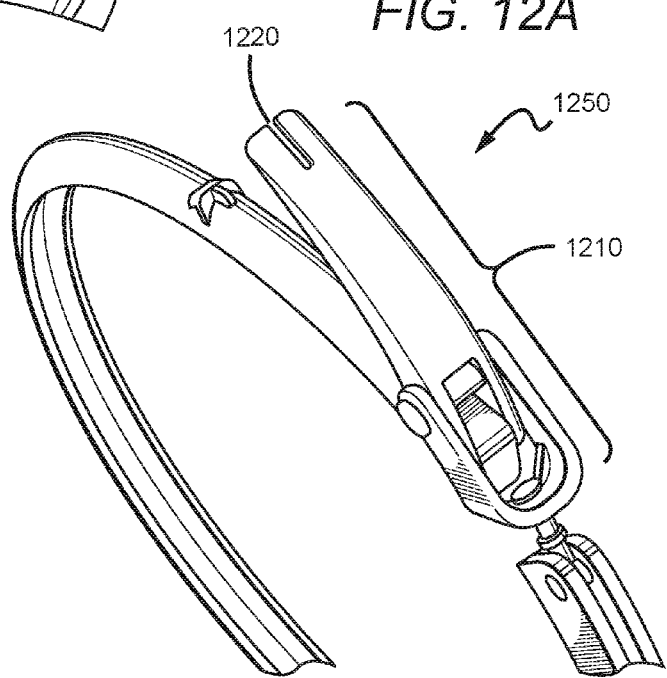
Figure 12B:
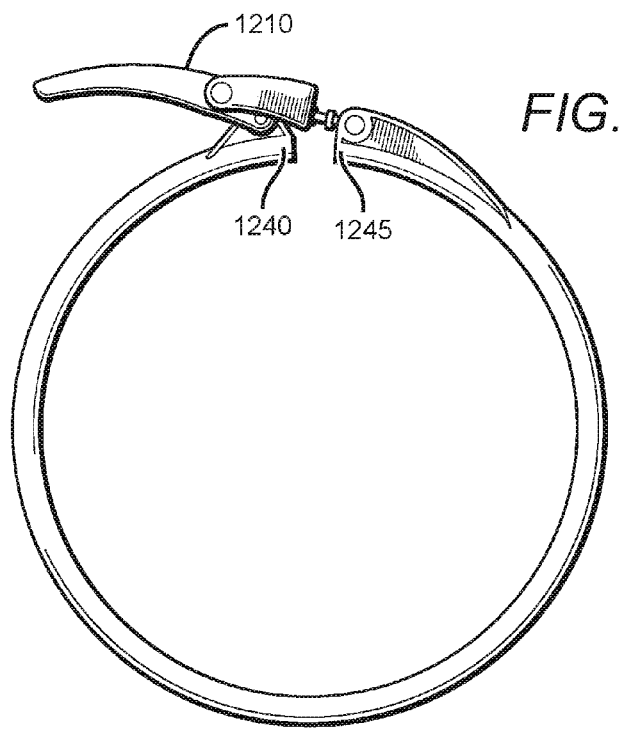
Figure 12C:
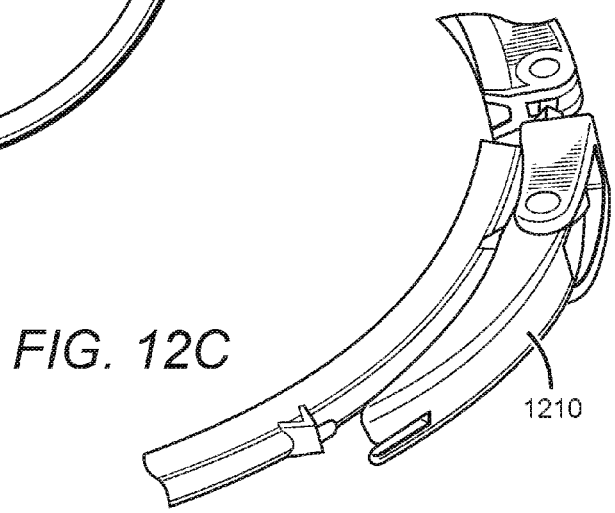
Figure 12D:
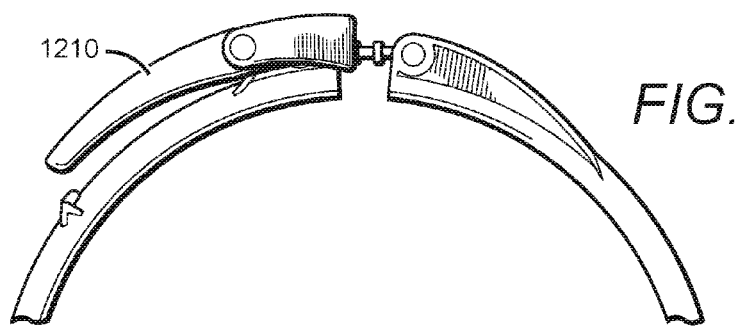

FIG. 9 is a side perspective view of an incubator chamber of the inventive subject matter showing a closed configuration wherein base flange 920 is in contact with lid flange 910. FIG. 10 is a side perspective view of the same incubator chamber in an open configuration wherein lid 1070 acts as a stable pedestal for base 1040 via legs 1050, 1060 and brim 1080, and wherein the base 1040 holds a first tray 1030, a second tray 1020, and a third tray 1010 substantially in place. Thus, FIGS. 9 and 10 show two ways in which components of an incubator chamber could be stacked upon one another. An astute reader would understand that incubator chambers of the inventive subject matter could be stackable such that 2, 5, 10, or even 25 or more incubator chambers could be stably stacked upon one another via base leg to lid brim connections. FIG. 11 provides a close up view of a base leg 1130 having a bottom portion 1120 that mages with brim 1110 of a corresponding lid.

FIGS. 12A-12E are different views of a clamp 1250 having an over the center latch handle 1210, a catch 1230, and a catch receiver 1220. Clamp 1250 could advantageously move between an open position (larger diameter) and a closed position (smaller diameter) by moving handle 1210 between an open position (e.g., FIG. 12B) and a closed position (e.g., FIG. 12C). It is contemplated that a first end 1240 and second end 1245 of catch 1250 could move closer or further away from one another based on a position of handle 1210 with respect to the rest of the clamp. The over center latch handle can comprise a lever mechanism and a locking portion comprising a catch receiver. A catch receiver can comprise a slit, a hook, or any other portion configured to receive a catch, while a catch can comprise any suitable component (e.g., protrusion, loop, hook) configured to releasably mate with the catch receiver. When the closure/handle has been adjusted such that the clamp tightly fits around a portion of the base and lid to substantially or completely seal the incubator chamber, the locking portion can be move towards the catch and releasably locked in place via a friction or other fit. It is contemplated that a user could readily release the lock in some embodiments with a single swipe of a finger or thumb.

As shown in FIG. 13, clamp 1250 could comprise an interior surface cavity sized and dimensioned to concurrently receive a lid flange and base flange in contact. For example, clamp 1250 could include a trapezoidal interior shape or cutout 1310.

FIG. 14 shows a lid 1410 and base 1430 approximated or held together via clamp 1420. In some embodiments a clamp is unnecessary to provide an air-tight seal. Where a clamp is provided, the clamp could be used to create a seal or stabilize a seal.

It should be appreciated that in some embodiments an entire incubator chamber (or substantial portions thereof) of the inventive subject matter could be made of material(s) to allow sterilization without removal of any component. It should also be appreciated that an incubator chamber of the inventive subject matter could be made of any suitable material or materials, including for example, a plastic (e.g., a thermoplastic, thermosetting polymer, etc.), a rubber, a silicon or a metal, and that the incubator chamber could be effective against leaks, defects or breakage.

FIG. 15 is a top view of a portion of a base including a gas distribution ramp 1510 including side walls sized and dimensioned to include a sensor seat 1520. The base further includes a gas inlet 1530 and gas outlet 1540 (and other ports) that are completely covered by a flange and sealing ring extending beyond a length of each of the ports. In other embodiments, it is contemplated that the gas ports could extend beyond a length of one or more flange(s).

FIG. 16 illustrates an outer wall of a gas distribution ramp including a wire, power or other communication port 1610 including a self-sealing membrane 1620 disposed therein. The self-sealing membrane 1620 (or removal of a lid) could allow a user to place a microscope, a $CO_2$ or other gas sensor, temperature sensor, wires, moisture sensor or any other object in an incubator chamber without breaking a seal between internal and external environments of the chamber.

Additionally or alternatively, a wireless or other device could be placed inside an incubator chamber of the inventive subject matter, which could continuously, or on demand, monitor one or more environmental conditions inside the unit.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An incubator chamber configured to provide an atmosphere-controlled environment, comprising:
   a base, a lid, and a clamp, wherein the base and lid define an interior space when coupled together;
   wherein the base comprises a first flange comprising an indentation sized and dimensioned to receive a sealing ring;
   wherein the base further comprises a gas distribution port coupled with a gas inlet and a gas outlet, and wherein the gas distribution port is fluidly coupled with a gas distribution portion having an upwardly slanted ramp, such that the gas distribution portion disrupts a flow of a gas from the gas inlet into the interior space;
   first and second trays disposed within the interior space;
   wherein the first tray comprises a bottom portion having a plurality of legs disposed about a perimeter of the first tray, wherein the legs extend downwardly from the bottom portion of the first tray, and wherein the plurality of legs are each sized to be placed between a pair of upwardly extending ribs of the base to prevent rotation of the first tray with respect to the base;
   wherein the second tray comprises a bottom portion having a second plurality of legs disposed about a perimeter of the second tray, which are sized and dimensioned to mate with an upward projection of the first tray, such that the second tray is stably stacked on top of the first tray by the second plurality of legs;
   wherein the lid comprises a second flange sized and dimensioned to mate with at least one of the first flange and the sealing ring of the base; and
   wherein the clamp comprises (a) an inner perimeter cavity sized and dimensioned to concurrently receive at least a portion of the first flange and at least a portion of the second flange, and (b) a levered locking mechanism that is configured to tighten the clamp about the at least the portion of the first flange and the at least the portion of the second flange.

2. The chamber of claim 1, wherein the first tray comprises a first leg and a second leg of the plurality of legs that cooperate with right and left sides of the gas distribution port, respectively, to prevent free rotation of the first tray.

3. The chamber of claim 1, wherein the base further comprises a depression positioned to facilitate removal of the sealing ring.

4. The chamber of claim 1, wherein each of the first flange and the second flange extend outwardly to completely overlie each of the gas inlet and the gas outlet.

5. The chamber of claim 1, wherein the lid comprises a top portion and a bottom portion, wherein the bottom portion comprises the second flange, wherein the top portion comprises a brim having a superior portion and an inferior portion, and wherein the brim extends around the entire perimeter of the top portion.

6. The chamber of claim 5, wherein a bottom portion of the base is sized and dimensioned to mate with the brim such that a sliding of the base is prevented when the lid is used as a pedestal for the base.

7. The chamber of claim 1, further comprising a communication port, and wherein the communication port comprises at least one of a wire port and a power port.

8. The chamber of claim 7, further comprising a self-sealing membrane disposed at the port.

9. The chamber of claim 1, wherein the clamp further comprises a catch and a catch receiver configured to releasably lock the clamp in a first position.

10. An incubator chamber configured to provide an atmosphere-controlled environment, comprising:
a base, and a lid, wherein the base and lid define an interior space when coupled together;
wherein the base comprises (a) a first flange comprising an annular indentation sized and dimensioned to receive a sealing ring, and (b) a depression positioned adjacent to the indentation to facilitate removal of the sealing ring; and
wherein the lid comprises a second flange sized and dimensioned to mate with at least one of the first flange and the sealing ring of the base;
wherein the base further comprises a gas distribution port coupled with a gas inlet and a gas outlet, and wherein the gas distribution port is fluidly coupled with a gas distribution portion having an upwardly slanted ramp, such that the gas distribution portion disrupts a flow of a gas from the gas inlet into the interior space;
first and second trays disposed within the interior space;
wherein the first tray comprises a bottom portion having a plurality of legs disposed about a perimeter of the first tray, wherein the legs extend downwardly from the bottom portion of the first tray, and wherein the plurality of legs are each sized to be placed between a pair of upwardly extending ribs of the base to prevent rotation of the first tray with respect to the base; and
wherein the second tray comprises a bottom portion having a second plurality of legs disposed about a perimeter of the second tray, which are sized and dimensioned to mate with an upward projection of the first tray, such that the second tray is stably stacked on top of the first tray by the second plurality of legs.

11. The chamber of claim 10, further comprising a clamp, wherein the clamp comprises (a) an inner perimeter cavity sized and dimensioned to concurrently receive at least a portion of the first flange and at least a portion of the second flange, and (b) a levered locking mechanism that is configured to tighten the clamp about the at least the portion of the first flange and the at least the portion of the second flange.

12. The chamber of claim 11, wherein the clamp further comprises a catch and a catch receiver configured to releasably lock the clamp in a first position.

13. The chamber of claim 10, wherein the first tray comprises a first leg and a second leg of the plurality of legs that cooperate with right and left sides of the gas distribution port, respectively, to prevent free rotation of the first tray.

14. The chamber of claim 10, wherein each of the first flange and the second flange extend outwardly to completely overlie each of the gas inlet and the gas outlet.

15. The chamber of claim 10, wherein the lid comprises a top portion and a bottom portion, wherein the bottom portion comprises the second flange, wherein the top portion comprises a brim having a superior portion and an inferior portion, and wherein the brim extends around the entire perimeter of the top portion.

16. The chamber of claim 15, wherein a bottom portion of the base is sized and dimensioned to mate with the brim such that a sliding of the base is prevented when the lid is used as a pedestal for the base.

17. The chamber of claim 10, further comprising a communication port, and wherein the communication port comprises at least one of a wire port and a power port.

18. The chamber of claim 17, further comprising a self-sealing membrane disposed at the port.

19. A set of chambers, comprising:
a first chamber as set forth in claim 1;
a second chamber as set forth in claim 1; and
wherein the base of the second chamber further comprises a third plurality of legs, each having a partially raised bottom portion that is configured to mate with a superior portion of a lid of the first chamber.

* * * * *